United States Patent [19]

Scheller, Jr. et al.

[11] 4,265,231
[45] May 5, 1981

[54] CURVED DRILL ATTACHMENT FOR BONE DRILLING USES

[76] Inventors: Arnold D. Scheller, Jr., 181 Essex St., North Quincy, Mass. 02171; Thomas B. Quigley, 99 Pond Ave., Brookline, Mass. 02146

[21] Appl. No.: 34,452

[22] Filed: Apr. 30, 1979

[51] Int. Cl.³ .............. A61F 5/04; A61F 17/32; E21B 7/04; E21B 7/08
[52] U.S. Cl. .............. 128/92 E; 128/92 EB; 128/305.1; 175/61; 175/75
[58] Field of Search ............ 64/2 R, 27 C, 27 CT; 128/92 EB, 92 E, 303 R, 305, 305.1, 312; 74/504; 175/61, 75

[56] References Cited

U.S. PATENT DOCUMENTS

| Re. 5,977 | 7/1874 | Welham | 64/2 R |
| Re. 13,884 | 2/1915 | Herzmark | 64/2 R |
| 550,783 | 12/1895 | Elliott et al. | 64/2 R |
| 887,160 | 5/1908 | Webb | 64/2 R |
| 4,057,115 | 11/1977 | Blanz | 64/2 R |

FOREIGN PATENT DOCUMENTS

| 2344267 | of 1977 | France | 128/92 EB |
| 20611 | of 1908 | United Kingdom | 175/75 |

OTHER PUBLICATIONS

Dremel ® Catalog for 1976, Dremel Mfg. Div. Emerson Elec. Co., Racine, Wis.
Air Instrument Surgery, vol. 1, 1970, Hall Pub. Inc., p. 217.

Primary Examiner—Robert W. Michell
Assistant Examiner—C. W. Shedd

[57] ABSTRACT

An attachment for a drill has a cannula attachable to the drill motor and provided with a curved distal portion. A flexible shaft extends through the cannula with a burr connected to its distal end and with its proximal end connectable to the drill motor to be rotated thereby.

11 Claims, 8 Drawing Figures

U.S. Patent  May 5, 1981  4,265,231
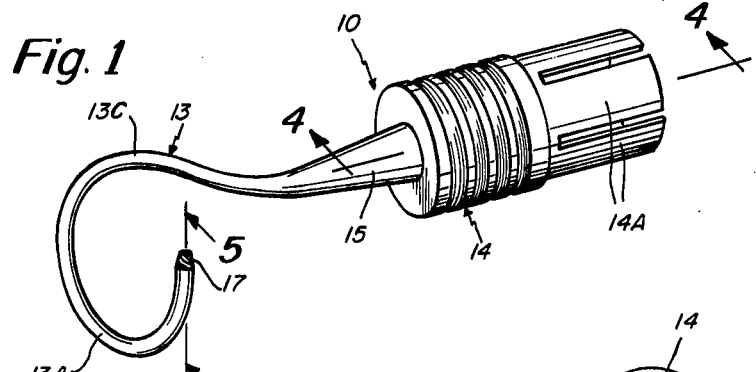
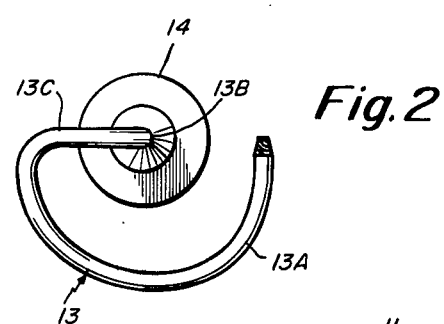
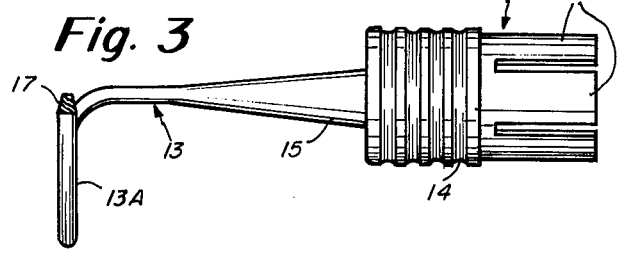
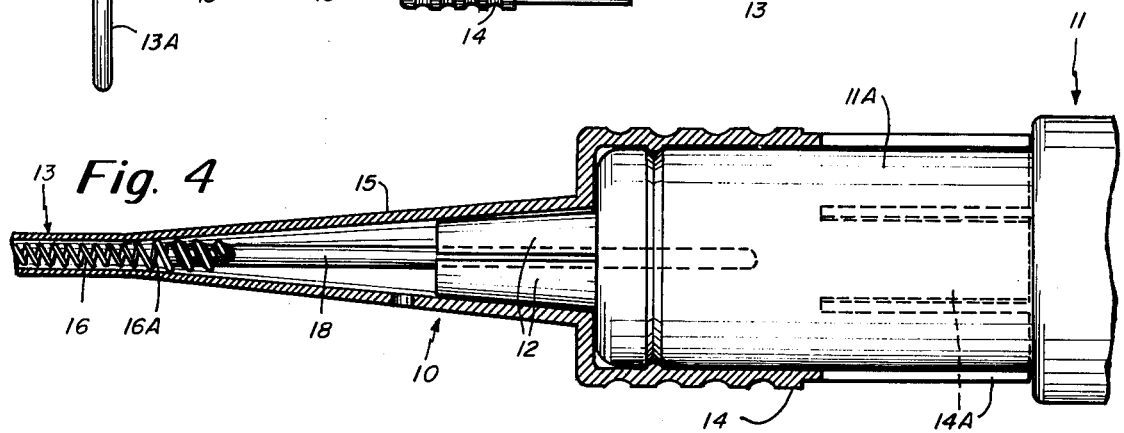
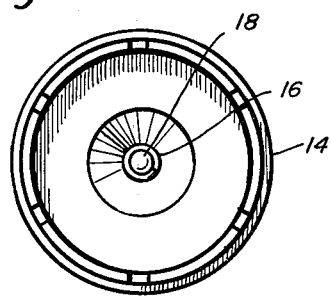
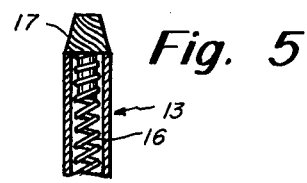
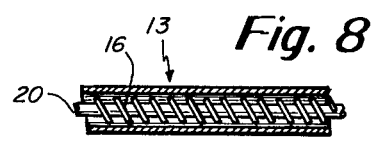

CURVED DRILL ATTACHMENT FOR BONE DRILLING USES

BACKGROUND OF THE INVENTION

In a substantial number of surgical procedures, it is necessary to drill through bone. By way of example, in order that a ligament may be secured in an appropriate location, the securing suture is passed by a needle through a straight bore in the bone and then held by an anchoring button for the necessary interval before the suture and button are removed.

Such a bore may be formed by using a straight drill but it is often desirable that the ends of the needle and suture passageway be non-aligned thus to enable them to be located relatively close one to the other. When this situation is encountered, two intersecting bores are made with a straight drill with the two bores defining an angle of less than 180°. The difficulty is that the more acute the angle defined by the intersecting bores, the more difficult it is to force the suture-carrying needle through the passageway, particularly if the diameter of the bores is held to a minimum and if the bone is relatively brittle.

A few examples of operations where the provision of a curved bore is advantageous are:

| REGION | | OPERATIONS |
| --- | --- | --- |
| A. Hand | 1. | Collateral ligament repairs |
| | 2. | Mallet finger deformity |
| | 3. | Volar plate reconstruction injuries |
| | 4. | Tenodesis in flexor profundus |
| B. Wrist | 1. | Radio-ulna dislocations |
| C. Elbow | 1. | Recurrent dislocations of the elbow (biceps transplant) |
| | 2. | Avulsed biceps tendon |
| D. Shoulder | 1. | Bankhardt repair of chronic dislocations of the shoulder |
| | 2. | Acromioclavicular separations |
| | 3. | Comminuted fractures of the humeral head |
| E. Spine | 1. | Posterior cervical fusions |
| F. Hip | 1. | Greater trochanteric reattachment |
| G. Knee | 1. | Cruciate reconstructions |
| | 2. | Quadriceps repair |
| | 3. | Patella fractures |
| | 4. | Popliteus tendon transfers |
| | 5. | Ligamentous reconstruction at the bone interface |
| H. Ankle | 1. | Ligamentous reconstruction procedures |
| I. Foot | 1. | Tenodesis and ligamentous reconstruction procedures |

THE PRESENT INVENTION

The general objective of the present invention is to provide an attachment for a drill motor, to enable a curved bore to be formed in and extend through a bone thus to enable a correspondingly curved needle with an attached suture to be readily passed through the bore.

In accordance with the invention, this objective is attained with a drill attachment for use in a substantial number of surgical procedures of which some have been referred to above. The attachment includes a rigid cannula, the proximal end of which is detachably attached to the drill motor housing and the distal portion of which is curved. A flexible shaft extends through the cannula with a proximal end portion connectable to the drill motor so as to be rotated thereby. A bone-cutting burr exposed at the distal end of the cannula is attached to the corresponding end of the flexible shaft.

Another objective of the invention is to provide a flexible shaft suitable for the small internal diameters of cannula that can be used for the purpose of the invention. In this connection, a drilled bore in a bone cannot exceed three-eighths of an inch in diameter. Bore dimensions are such that a correspondingly curved suture needle may be passed freely through the curved bore. In general, the smaller the curved bore, for any particular surgical procedure, the better. This objective is attained by the use of a stretched coil spring with the proximal end portion of the shaft a length of drill rod to which one end of the spring is anchored and the burr secured to the other end of the spring. The proximal end of the cannula is enlarged and the turns of the spring therein are of increased diameter thereby providing means yieldably holding the burr in position. The spring may be provided with an internal reinforcement.

Yet another objective of the invention is to ensure that the attachment can be safely used even where the envolved bone is relatively brittle, an objective attained by providing that the curved distal portion of the cannula is in a plane normal to the axis of the proximal end of the shaft and concentric therewith thus to enable the surgeon to advance the burr by turning the wrist of his hand by which the drill is held and a particular objective of the invention is to enable the curved distal portion of the attachment to be of an adequate extent, an objective attained with the cannula including an intermediate portion that extends forwardly and outwardly with respect to its proximal end.

BRIEF DESCRIPTION OF THE DRAWINGS

The accompanying drawings illustrate a preferred embodiment of a drill attachment in accordance with the invention.

Of the drawings

FIG. 1 is a perspective view of the attachment;

FIG. 2 is a burr end view thereof;

FIG. 3 is a side view of the attachment; FIG. 4 is a section, on an increase in scale, taken approximately along the indicated line 3—3 of FIG. 1 and including a portion of a drill;

FIG. 5 is a fragmentary section taken approximately along the indicated line 5—5 of FIG. 1;

FIG. 6 is a hub-end view of the attachment on the scale of FIG. 3;

FIG. 7 is a lengthwise section of a portion of a cannula illustrating a flexible shaft provided with an internal reinforcement in the form of a coil spring of the hand opposite to that of the spring it reinforces; and FIG. 8 is a like view but with the reinforcement in the form of a flexible, small diameter core of a suitable plastic.

THE PREFERRED EMBODIMENT OF THE INVENTION

The curved drill attachment illustrated by the drawings is generally indicated at 10 and is particularly adapted for use with an air-turbine power system such as the drill motor, generally indicated at 11 and provided with jaws 12 adjustable to grip or release a burr. One source of such drill motors is Amsco/Hall Surgical, a Division of American Sterilizer Company and located at Santa Barbara, Cal.

The attachment 10 has a curved rigid stainless steel cannula generally indicated at 13, a hub 14 and a tapered chamber section 15 which is shown as a unitary part of the cannula but which may be separately formed. The hub 14 fits on the end 11A of the housing of the drill motor 11 and has resilient gripping fingers 14A to ensure its firm retention. The chamber section 15 is dimensioned freely to receive the jaws 12 of the drill motor 11. Stainless steel cannula is available in a suitable size range and that having an outside diameter of 0.094 inch and an inside diameter of 0.070 inch has proved satisfactory in use.

A flexible shaft extends through the cannula 13 and consists of a stainless steel coil spring 16 coated with a suitable lubricant such as Teflon and stretched within the cannula 13 with one end anchored to a burr 17 exposed at the distal end of the cannula 13. The other end of the spring 16 extends into the chamber section 15 where it is secured to a length of a drill rod 18 which is exposed to enter between the drill jaws 12 when the attachment is fitted on the drill motor 11 and then to be locked to the jaws 12 when the jaw operating means, not shown, are operated. The spring is of the hand relative to the direction the shaft is to be rotated by the drill motor to effect the application of torque to the burr 17. The diameter of the turns of the spring 16 is increased in that portion within the chamber section 15 and where it is soldered to the rod 18 thereby providing a section 16A by which movement of the burr 17 away from the distal end of the cannula is resiliently opposed and by which the rod 18 is held. A coil spring that has proved satisfactory has an unstretched diameter of its turns of 0.062 inch and a wire diameter of 0.012 inch.

It has been found that a burr having a diameter of 0.110 inch is satisfactory for use in all operations of which those previously referred to are examples even where the bones are small such as those of a hand. An attachment with a burr of, say, 0.078 inch in diameter is more ideal for drilling curved bores in such small bones and can also be used where the bones are large. Smaller burrs of course require that the diameter of the cannula used be less than that of the selected burr size. Burr sizes are within the approximate range of 0.25 to 0.050 inch.

The cannula 13 includes a distal portion 13A that is arcuate with respect to the axial proximal portion 13B and an intermediate portion 13C that is forwardly and outwardly curved and then forwardly and inwardly curved in order that the distal portion 13A may be in the neighborhood of 180° in extent and have a desired radius, five-tenths of an inch by way of a preferred example and not of limitation.

In cases where reinforcement of the spring 16 is desirable, internal reinforcement therefor may be effected, as illustrated by FIG. 7, by a coil spring 19 of opposite hand or, as shown in FIG. 8, by a flexible core 20 of a suitable plastic such as Teflon, for one example.

With an attachment in accordance with the invention secured to a drill motor, a surgeon is able to provide a curved bore through a bone by turning the wrist of the hand holding the drill thus minimizing bone stress and then easily to pass a curved needle (not shown) of a corresponding curvature through the passageway to draw a suture into position as required in various operations such as those previously referred to.

We claim:

1. A drilling attachment for a drill motor having rotatable means operable to grip or release a burr or drill, said attachment for use in surgical procedures requiring a passageway through bone with the ends of the passageway not in alignment, said attachment including a rigid cannula including a proximal end portion a having a longitudinal axis, said proximal end portion being attachable to the housing of a drill motor and freely receptive of the gripping means thereof, a curved intermediate portion of said cannula extending radially with respect to said longitudinal axis, and a curved distal portion of said cannula lying in a plane which is perpendicular to said longitudinal axis of said proximal portion and substantially concentric with respect to said axis, a bone-cutting burr exposed at the distal end of said distal portion, and a burr-rotating flexible shaft within said cannula, said shaft being anchored to said burr at said distal end and attached to a rod at said proximal end, which rod is connectable to said rotatable gripping means of said drill motor, whereby said drilling attachment and said burr are dimensioned in such fashion that when used a passageway is provided through a bone appropriate for the passage of a curved surgical needle therethrough.

2. The drilling attachment of claim 1 in which the concentrically curved distal portion of the cannula subtends an arc approximately 180° in extent.

3. The drilling attachment of claim 1 in which the flexible shaft includes a stretched coiled spring which spring is of the hand relative to the direction the shaft is rotated by the drill motor to effect the application of torque to the burr.

4. The drilling attachment of claim 3 in which the portion of the cannula adjacent said proximal end is of increased diameter freely to accommodate the shaft securing means of the drill motor, and the turns of the coil spring in said portion of increased diameter are also of increased diameter, said spring being so sized in length to yieldably oppose movement of said burr away from the distal end of the cannula.

5. The drilling attachment of claim 3 wherein said flexible shaft is further comprised of an internal reinforcement for the coil spring extending lengthwise thereof between the rod and the burr but unattached thereto.

6. The drilling attachment of claim 5 in which the internal reinforcement is a coil spring of the hand opposite to that of the spring it reinforces.

7. The drilling attachment of claim 5 in which the internal reinforcement is a small diameter flexible plastic rod.

8. The drilling attachment of claim 1 in which the burr diameter is in the approximate range 0.050 to 0.25 inch.

9. The drilling attachment of claim 1 in which the outside diameter of the cannular is close to that of the burr.

10. The drilling attachment of claim 1 in which the intermediate portion of the cannula is disposed so as to space the distal end from the proximal end.

11. The drilling attachment of claim 1 in which the distal end of the intermediate portion of the cannula is located at a greater radial distance from said longitudinal axis than any part of the proximal end portion.

* * * * *